US006692252B2

(12) United States Patent
Scott

(10) Patent No.: US 6,692,252 B2
(45) Date of Patent: Feb. 17, 2004

(54) HEAT SINK WITH GEOMETRIC ARRANGEMENT OF LED SURFACES

(75) Inventor: Robert R. Scott, Riverton, UT (US)

(73) Assignee: Ultradent Products, Inc., South Jordan, UT (US)

(*) Notice: Subject to any disclaimer, the term of this patent is extended or adjusted under 35 U.S.C. 154(b) by 149 days.

(21) Appl. No.: 10/024,110

(22) Filed: Dec. 17, 2001

(65) Prior Publication Data
US 2003/0113684 A1 Jun. 19, 2003

(51) Int. Cl.$^7$ .................................................. A61C 3/00
(52) U.S. Cl. ......................................................... 433/29
(58) Field of Search .......................... 433/29; 362/553, 362/555, 572, 573, 294, 580

(56) References Cited

U.S. PATENT DOCUMENTS

| | | |
|---|---|---|
| 4,935,665 A | 6/1990 | Murata |
| 4,963,798 A | 10/1990 | McDermott |
| 4,989,217 A | 1/1991 | Ostler ........................ 372/107 |
| 5,214,658 A | 5/1993 | Ostler ........................ 372/23 |
| 5,233,283 A | 8/1993 | Kennedy ..................... 320/13 |
| 5,420,768 A | 5/1995 | Kennedy ..................... 362/119 |
| 5,457,611 A | 10/1995 | Verderber |
| 5,550,853 A | 8/1996 | Ostler ........................ 372/34 |
| 5,634,711 A | 6/1997 | Kennedy et al. ............. 362/119 |
| 5,660,461 A | 8/1997 | Ignatius et al. ............. 362/241 |
| 5,698,866 A | 12/1997 | Doiron et al. ................ 257/99 |
| 5,782,553 A | 7/1998 | McDermott |
| 5,803,729 A | 9/1998 | Tsimerman |
| 5,890,794 A | 4/1999 | Abtahi et al. |
| 6,331,111 B1 | 12/2001 | Cao ........................... 433/29 |
| 6,468,077 B1 | 10/2002 | Melikechi et al. |
| 6,482,004 B1 | 11/2002 | Senn et al. |
| 2001/0038992 A1 | 11/2001 | Otsuka |
| 2001/0046652 A1 | 11/2001 | Ostler et al. |
| 2002/0093833 A1 | 7/2002 | West |
| 2002/0115037 A1 | 8/2002 | Cao ........................... 433/29 |
| 2002/0133970 A1 | 9/2002 | Gordon et al. |
| 2002/0163317 A1 | 11/2002 | Cao ........................... 315/291 |
| 2002/0167283 A1 | 11/2002 | Cao ........................... 315/291 |
| 2002/0168603 A1 | 11/2002 | Cao ........................... 433/29 |
| 2002/0168604 A1 | 11/2002 | Cao ........................... 433/29 |
| 2002/0168605 A1 | 11/2002 | Cao ........................... 433/29 |
| 2002/0168606 A1 | 11/2002 | Cao ........................... 433/29 |
| 2002/0168607 A1 | 11/2002 | Cao ........................... 433/29 |

(List continued on next page.)

FOREIGN PATENT DOCUMENTS

WO     WO 99/35995     7/1999

OTHER PUBLICATIONS

U.S. patent application Ser. No. 10/016,992, Cao, filed Dec. 13, 2001.
U.S. patent application Ser. No. 10/017,454, Cao, filed Dec. 13, 2001.

(List continued on next page.)

Primary Examiner—Todd E. Manahan
(74) Attorney, Agent, or Firm—Workman Nydegger

(57) ABSTRACT

A heat sink for a dental light-curing device comprises three mounting surfaces that are each configured for mounting a light source, such as an LED or LED array, which is capable of generating light suitable for curing light-curable compounds. The mounting surfaces are configured with a geometric arrangement in which one of the mounting surfaces is placed nearer to the tip of the heat sink than either of the remaining two mounting surfaces, which are placed adjacent to the first mounting surface and are spaced an equal distance away from the tip of the heat sink. This arrangement generally minimizes the heat that is generated by the LEDs at the tip of the heat sink and expedites the diffusion of heat from the LEDs.

28 Claims, 2 Drawing Sheets

U.S. PATENT DOCUMENTS

| | | | |
|---|---|---|---|
| 2002/0168608 A1 | 11/2002 | Cao | 433/29 |
| 2002/0172912 A1 | 11/2002 | Cao | 433/29 |
| 2002/0172913 A1 | 11/2002 | Cao | 433/29 |
| 2002/0172914 A1 | 11/2002 | Cao | 433/29 |
| 2002/0172915 A1 | 11/2002 | Cao | 433/29 |
| 2002/0172916 A1 | 11/2002 | Cao | 433/29 |
| 2002/0172917 A1 | 11/2002 | Cao | 433/29 |
| 2002/0175352 A1 | 11/2002 | Cao | 257/258 |
| 2002/0175628 A1 | 11/2002 | Cao | 315/56 |
| 2002/0177095 A1 | 11/2002 | Cao | 433/29 |
| 2002/0177096 A1 | 11/2002 | Cao | 433/29 |
| 2002/0177099 A1 | 11/2002 | Cao | 433/29 |
| 2002/0180368 A1 | 12/2002 | Cao | 315/149 |
| 2002/0181947 A1 | 12/2002 | Cao | 392/409 |
| 2002/0182561 A1 | 12/2002 | Cao | 433/29 |
| 2002/0182562 A1 | 12/2002 | Cao | 433/29 |
| 2002/0190659 A1 | 12/2002 | Cao | 315/149 |
| 2002/0190660 A1 | 12/2002 | Cao | 315/149 |
| 2002/0197582 A1 | 12/2002 | Cao | 433/29 |
| 2003/0001507 A1 | 1/2003 | Cao | 315/56 |
| 2003/0038291 A1 | 2/2003 | Cao | 257/81 |
| 2003/0039119 A1 | 2/2003 | Cao | 362/227 |
| 2003/0039120 A1 | 2/2003 | Cao | 362/227 |
| 2003/0039122 A1 | 2/2003 | Cao | 362/294 |
| 2003/0040200 A1 | 2/2003 | Cao | 438/800 |

OTHER PUBLICATIONS

U.S. patent application Ser. No. 10/017,455, Cao, filed Dec. 13, 2001.

U.S. patent application Ser. No. 10/017,272, Cao, filed Dec. 13, 2001.

U.S. patent application Ser. No. 10/067,692, Cao, filed Feb. 4, 2002.

U.S. patent application Ser. No. 10/071,847, Cao, filed Feb. 6, 2002.

U.S. patent application Ser. No. 10/072,302, Cao, filed Feb. 5, 2002.

U.S. patent application Ser. No. 10/072,462, Cao, filed Feb. 5, 2002.

U.S. patent application Ser. No. 10/072,613, Cao, filed Feb. 5, 2002.

U.S. patent application Ser. No. 10/072,635, Cao, filed Feb. 5, 2002.

U.S. patent application Ser. No. 10/072,659, Cao, filed Feb. 5, 2002.

U.S. patent application Ser. No. 10/072,826, Cao, filed Feb. 5, 2002.

U.S. patent application Ser. No. 10/072,831, Cao, filed Feb. 6, 2002.

U.S. patent application Ser. No. 10/072,850, Cao, filed Feb. 5, 2002.

U.S. patent application Ser. No. 10/072,852, Cao, filed Feb. 6, 2002.

U.S. patent application Ser. No. 10/072,853, Cao, filed Feb. 5, 2002.

U.S. patent application Ser. No. 10/072,858, Cao, filed Feb. 5, 2002.

U.S. patent application Ser. No. 10/072,859, Cao, filed Feb. 5, 2002.

U.S. patent application Ser. No. 10/073,672, Cao, filed Feb. 11, 2002.

U.S. patent application Ser. No. 10/073,819, Cao, filed Feb. 11, 2002.

U.S. patent application Ser. No. 10/073,822, Cao, filed Feb. 11, 2002.

U.S. patent application Ser. No. 10/073,823, Cao, filed Feb. 11, 2002.

U.S. patent application Ser. No. 10/076,128, Cao, filed Feb. 12, 2002.

U.S. patent application Ser. No. 60/304,324, Cao, filed Jul. 10, 2001.

"NRG L.E.D. Curing Light", Denstply Caulk (2001).

HEAT SINK WITH GEOMETRIC ARRANGEMENT OF LED SURFACES

BACKGROUND OF THE INVENTION

1. The Field of the Invention

The present invention generally relates to the field of light curing devices incorporating LED light sources and, more particularly, to the field of heat sinks configured for dissipating heat generated by the light sources of the light curing devices.

2. The Relevant Technology

In the field of dentistry, dental cavities are often filled and/or sealed with photosensitive compounds that are cured when they are exposed to radiant energy, such as visible or ultraviolet light. These compounds, commonly referred to as light-curable compounds, are placed within dental cavity preparations or onto dental surfaces where they are subsequently irradiated by a light-curing dental device.

Many light-curing devices are configured with a fiber optic light wand for directing light from a light source into a patient's mouth. The light source may comprise, for example, a lamp, a halogen bulb or a light-emitting diode (LED). One end of the light wand is placed close to the light source so that the light emitted from the light source will be directed into the light wand. One problem with light wands, however, is that they are generally unable to capture all of the light that is generated by the light source, particularly the light that is emitted from LEDs, which may be emitted at angles of up to about 120°.

One method for overcoming the limitations of light capture by light wands and for generally improving the efficiency of the light-curing devices is to place the light source(s) of a light-curing device at the tip of the light-curing device. This enables all of the light generated by the light source(s) to be directed within the patient's mouth, at the desired application site. Although this generally overcomes the aforementioned problems associated with light wands, the proximity of the light source to the patient's mouth can create a new problem. In particular, the heat that is generated by the light source(s) at the tip of the light-curing device can create discomfort to the patient when the tip of the light-curing device happens to come in contact or immediate proximity to the sensitive mouth tissues of the patient. Accordingly, it is desirable to minimize the heat at the tip of the light-curing device.

One method for minimizing the heat at the tip of the light-curing device is to mount the light source(s) on a heat sink that can generally conduct the heat away from the tip of the light-curing device. Heat sinks, which operate on the principles of conduction and convention, are well known in the art of thermodynamics. As is commonly understood, the ability of a heat sink to diffuse heat is generally controlled by the material properties and geometries of the heat sink. The arrangement and geometries of the mounting surfaces of the heat sink are also important factors to consider when determining how efficiently the heat sink is able to diffuse heat.

Recently, light-curing devices have been developed that utilize multiple light sources. One such design incorporates a plurality of LEDs that are spaced apart and mounted on opposing angled surfaces of the heat sink. This design is particularly useful because it enables the plurality of LEDs to generally surround and simultaneously irradiate dental cavity preparations and other application sites from a variety of angles. One disadvantage of this design, however, is that each of the multiple LEDs generate heat that must be diffused. Although a heat sink is incorporated within this multiple LED design, the arrangement of the LEDs and LED mounting surfaces is not conducive to the efficient diffusion of the heat. Rather, the arrangement of LEDs is such that a majority of heat is generated and accumulated at the tip of the heat sink, where it is logistically the most difficult to diffuse. In fact there is no existing heat sink for light-curing devices comprising a geometric arrangement of three mounting surfaces that is specifically designed to increase the efficiency of the heat sink, rather than relying solely on the thermally conductive properties of the heat sink.

Accordingly, in view of the foregoing, there is currently a need in the art for improved heat sinks for dental light-curing devices that comprise mounting surfaces that are configured in geometric arrangements conducive to the diffusion of heat generated by LEDs mounted thereon.

SUMMARY OF PRESENTLY PREFERRED EMBODIMENTS

Briefly summarized, presently preferred embodiments of the present invention are directed to heat sinks for dental light-curing devices comprising LED mounting surfaces arranged in geometric configurations conducive to the diffusion of heat generated by the LEDs.

According to one presently preferred embodiment, a heat sink comprises three mounting surfaces configured for mounting three corresponding light sources. The heat sink may comprise any material having a conduction coefficient that facilitates the conduction of heat. Suitable materials include, but are not limited to any combination of aluminum, copper, silver, other metals, and other materials with high conduction coefficients.

The heat sink is preferably configured in size and shape to be inserted within a handheld dental light-curing device. According to one presently preferred embodiment, the heat sink comprises a body that has a generally cylindrical cross-sectional area. The diameter of the heat sink is preferably between about 0.25 inches and about 0.75 inches. The length of the heat sink, which extends between a proximal end and a distal end of the heat sink, is preferably between about 1 inch and about 6 inches. It will be appreciated, however, that the length, width and cross-sectional area of the body may vary to accommodate any desired configuration.

According to the preferred embodiment, the three mounting surfaces of the heat sink are disposed on a face that is located near the distal end of the heat sink. Each of the mounting surfaces is configured for mounting an LED light source, which may comprise a single LED, an LED array, or any combination of LEDs. The mounting surfaces of the heat sink may also be configured to mount any other light source that is capable of generating light suitable for curing light-curable compounds.

The three mounting surfaces preferably comprise planar surfaces that converge at a central intersection point that is recessed into the body, such that the face is approximately concaved. The surface-to-surface angle that occurs between any two of the planar surfaces is preferably an angle within a range of about 100° and about 140°, with a most preferred angle of approximately 120°.

The three mounting surfaces are configured in a geometric arrangement that is specifically configured for minimizing the heat generated by the LEDs at the distal end of the heat sink, and which is generally conducive to the diffusion of heat generated by the LEDs.

According to one preferred embodiment, the mounting surfaces are symmetrically disposed on the face, with one of the three mounting surfaces disposed on a distal portion of the face and the two remaining mounting surfaces disposed on a proximal portion of the face. It will be appreciated that this arrangement causes one of the three mounting surfaces to be located closer to the distal end of the body than either of the two remaining mounting surfaces, which are preferably spaced an equal distance away from the distal end of the body. According to the preferred embodiment, the symmetry of the face is also aligned with the symmetry of the body, such that a line of symmetry extending between the two proximal mounting surfaces lies substantially parallel with a central axis of the heat sink.

It will be appreciated, however, that according to another embodiment, the line of symmetry of the face may be angularly offset from the central axis of the heat sink, such that the two proximal mounting surfaces are not spaced equally away from the distal end. It is also within the scope of the invention for the mounting surfaces to be asymmetrically spaced apart or aligned.

According to the preferred embodiment, each of the LED light sources mounted on the three mounting surfaces generates substantially equal amounts of light and heat. Therefore, the heat generated by the LED light sources that are mounted on the two mounting surfaces that are the furthest away from the distal end of the tip will be collectively greater than the heat that is generated by the LED light source that is mounted on the mounting surface adjacent to the distal end. Therefore, it will be appreciated that the geometric arrangement of the mounting surfaces of the inventive heat sink causes a majority of the heat that is generated by the three LED light sources to be generated near the body of the heat sink where the heat is more easily diffused through the body and away from the distal end of the heat sink body, rather than at the distal end, where it is logistically more difficult to diffuse the heat.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the heat sink of the invention will now be provided with specific reference to figures illustrating preferred embodiments of the invention. It will be appreciated that like structures will be provided with like reference designations.

To provide assistance in construing the scope of the invention, the following definitions are provided. The term "face," as used herein, generally refers to the portion of the heat sink configured for mounting light sources. In particular, the face includes a plurality of mounting surfaces that are each configured for mounting a separate light source.

The term "light source," as used herein, generally refers to any source of light that is capable of providing radiant energy suitable for curing light curable compounds. A light source may include, for example, but is not limited to an individual LED or an LED array. The light sources are disposed on the mounting surfaces of the face.

According to the invention, the face is generally divided equally into two portions, namely, a "proximal portion" or "half" and a "distal portion" or "half". The division between the proximal half and the distal half occurs at the approximate center of the face, in terms of length, when the length of the face is measured parallel with the axis of the heat sink. Although the surface area and volume of the proximal half and the distal half may be the same according to certain embodiments, they are not necessarily the same according to all embodiments of the invention. They are, however, the same length.

Figure 1:
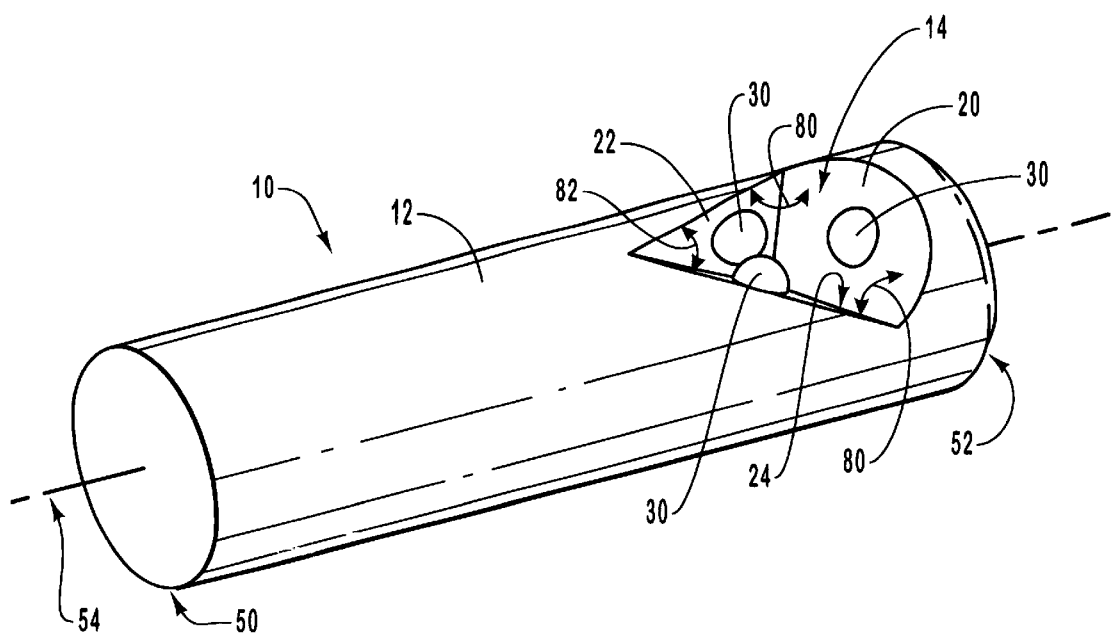
FIG. 1 illustrates a perspective view of one embodiment of the heat sink of the invention that includes an individual LED mounted on each of the three mounting surfaces of the heat sink.
Figure 2:
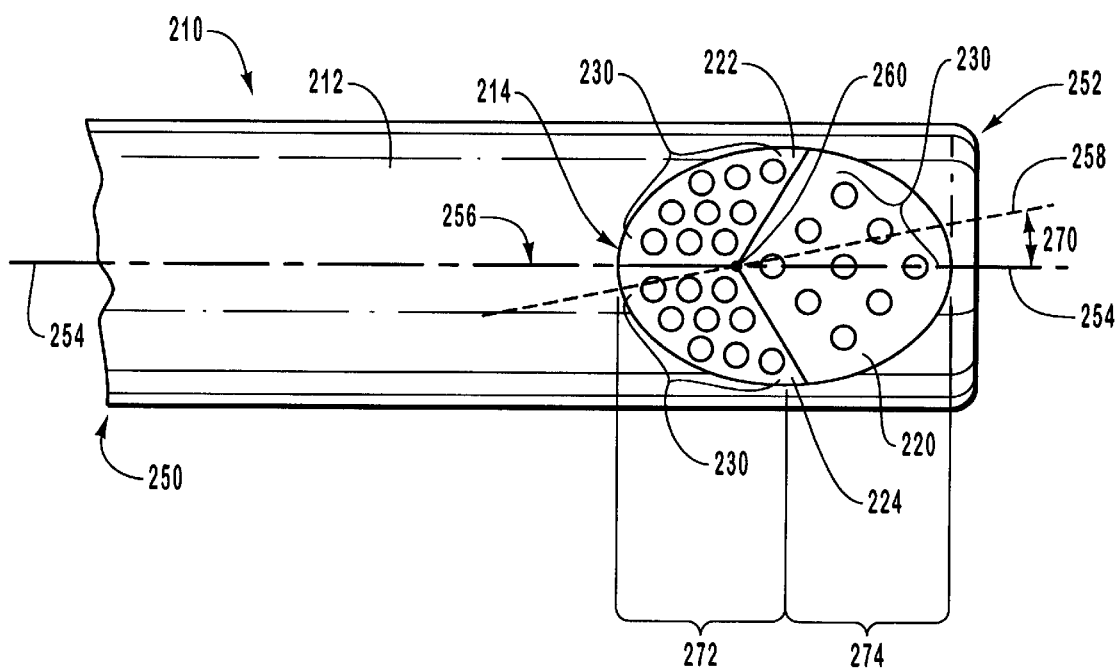
FIG. 2 illustrates a top view of one embodiment of the heat sink of the invention that includes LED arrays mounted on each of three mounting surfaces.

Reference is first made to FIG. 1, which illustrates a perspective view of one embodiment of the heat sink 10 of the invention, which includes a body 12, a face 14, and three mounting surfaces 20, 22, 24 that are disposed on the face. According to the invention, each of the mounting surfaces 20, 22, 24 comprises a light source 30 capable of generating light for irradiating a light-curable compound with radiant energy. One suitable light source 30 comprises an LED. As shown in FIG. 2, the light source 230 may also comprise an LED array. Other suitable light source for irradiating light-curable compounds can also be used.

Light sources 30 and 230 generate light that is desirable and necessary for curing light-curable compounds. However, they also generate heat which is undesirable and which can create discomfort to a patient when the light sources 30 and 230 come in contact or immediate proximity to a patient's sensitive mouth tissue. Accordingly, it is desirable to diffuse at least some of the heat that is generated by the light sources 30 and 230 during use.

Figure 4:
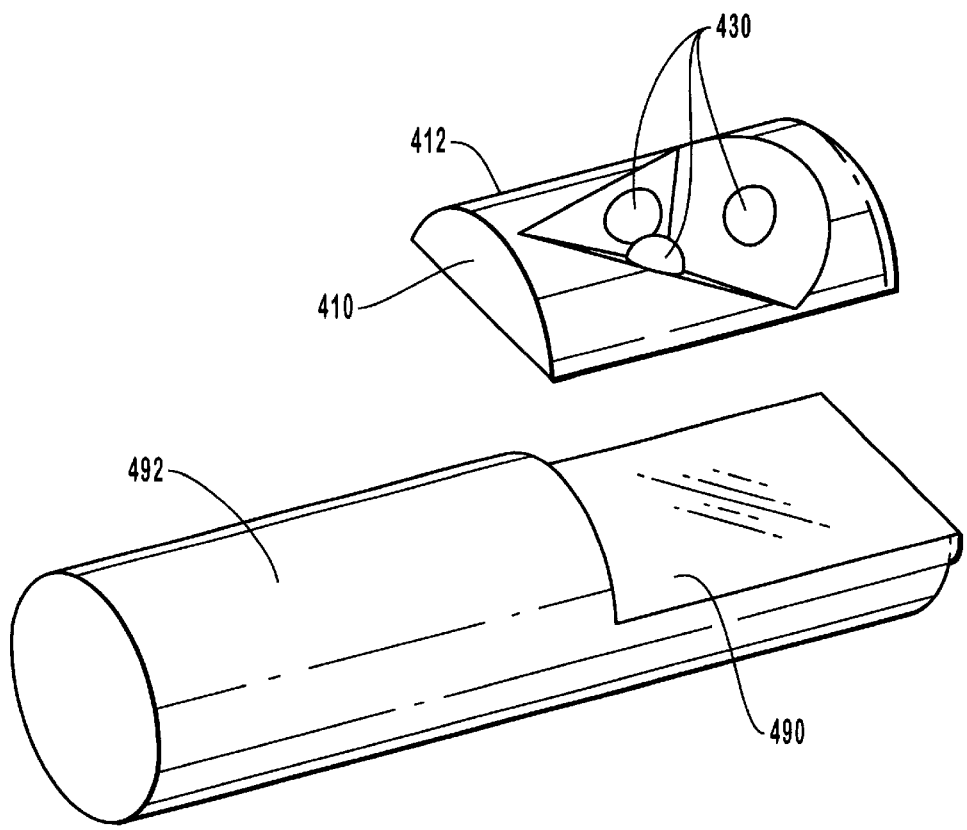
FIG. 4 illustrates a perspective view of one embodiment of the heat sink of the invention in which the heat sink comprises a semi-circular cross-sectional area configured for being mounted onto the flat surface of a secondary heat sink, which is also shown.

One method for diffusing heat is through a heat sink, such as heat sink 10. According to the preferred embodiment, as shown in FIG. 1, heat sink 10 extends longitudinally from a proximal end 50 to a distal end 52, with a central axis 54 extending centrally therebetween. As shown, the body 12 of the heat sink 10 may comprise a substantially cylindrical shape. The cylindrical shape may be desirable, for example, to maximize a cross-sectional area of the heat sink within a handheld dental light-curing device. It will be appreciated, however, that the heat sink 10 may also comprise other body types. By way of example and not limitation, as shown in FIG. 4, the cross-sectional shape of body 412 can be hemispheric, as well as any other desired shape. Different shapes, may be desired, for example, to maximize the space that is available within differently shaped light-curing devices. Other types of shapes that can be incorporated by the heat sinks of the invention include, but are not limited to hexagonal, triangular, oval, and square.

According to one preferred embodiment of the invention, the light sources 30 of the heat sink 10 are substantially equally spaced apart on the face 14 of the heat sink 10 and they each generate a substantially equal amount of light. This configuration is preferred because it enables the light generated by the light sources 30 to be uniformly and simultaneously applied to a desired application site from various directions. It will be appreciated that inasmuch as the light generated by each of the light sources 30 is substantially equal, the heat generated by each of the light sources 30 will also be substantially equal.

It is desirable to minimize the heat that is generated by the light sources 30 at the tip 52 of the heat sink. Heat can generally be diffused from the tip 52 in one of two ways. The first comprises conduction and generally involves the transfer of heat through a solid. For example, according to the principles of conduction, heat sink 10 transfers heat from light sources 30, through the body 12, and to the cooler regions of the body 12 where the heat is generally diffused.

The second way in which heat is diffused by heat sink 10 is through convection. Convection generally involves the transfer of heat from a solid to a gas, such as the air. It will be appreciated by those skilled in the art of thermodynamics that conduction is much more efficient than convection. Accordingly, it is desirable to increase the transfer rate of the heat from the light sources 30 to the cooler regions of the body 12. One way to speed up the conductive transfer of heat through the heat sink 10 is to manufacture the heat sink 10 out of materials with a high conduction coefficient, such as Aluminum, Copper, and Silver. Aluminum is especially preferred because it is lightweight, malleable and relatively inexpensive. It will be appreciated, however, that heat sink 10 of the invention, can be composed of any thermally conductive material.

Another method for increasing the transfer rate of heat from the light sources 30 to the cooler regions of the body 12 is to minimize the distance the heat has to travel through the body 12 of the heat sink 10 before it is diffused. The present invention accomplishes this by configuring the mounting surfaces and corresponding light sources in a geometric arrangement that places two of the three LED mounting surfaces, 22 and 24, at the proximal portion of the face 14 and only a single LED mounting surface 20 at the distal portion of the face 14. It will be appreciated that this geometric arrangement generally minimizes the heat that is generated at the tip, or distal end 52, of the heat sink 10, while at the same time minimizing the distance in which the majority of the heat generated by the light sources 30 has to travel before it is diffused by the body 12 of the heat sink 10, thereby maximizing the efficiency of the heat sink 10.

One preferred arrangement of the mounting surfaces 220, 222, 224 is shown in FIG. 2. As shown, the arrangement of the mounting surfaces 220, 222, 224 on the face 214 is generally symmetric, such that a line of symmetry 256 extends between the two proximally located mounting surfaces 222 and 224 and bisects the third mounting surface 220. According to the preferred embodiment, the symmetry of the face 214 and corresponding mounting surfaces 220, 222, 224 are oriented in alignment with the symmetry of the heat sink body 212, such that the line of symmetry 256 is substantially parallel with the central axis 254 of the heat sink 212. It will be appreciated that this generally ensures that the two proximally located mounting surfaces 222 and 224, located at the proximal face portion 272, are spaced an equal distance away from the distal end 252 of the heat sink 212, which is useful for ensuring that the heat generated at mounting surfaces 222 and 224 is conducted away from the distal end 252 of the heat sink 212 and diffused at a substantially equal rate. It will also be appreciated that this minimizes the distance in which the heat must travel through the heat sink 10 before arriving at the cooler regions of the body 12, where the heat is diffused, thereby increasing the efficiency of the heat sink 10.

Although alignment of the face 214 and the body 212 is preferred, it will be appreciated that the alignment of the face 214 can also be angularly offset from the symmetry of the body 212. For example, according to one alternative embodiment, not shown, the face 214 can be oriented along any alternative line of symmetry, such as line 258, which is angularly offset from the central axis 254 of the body 212 by a predetermined angle 270. It is desirable, however, that within any alternative embodiment of the invention that the majority of light sources 230 are disposed on the proximal face portion 272 and that a minimal number of light sources 230 are disposed on the distal face portion 274, to minimize the heat that is generated at the distal face portion 274, as mentioned above.

Although the previous examples go into some detail regarding the symmetry of the face 214, it will be appreciated that it is within the scope of the invention for the mounting surfaces 220, 222, 224 to be asymmetrically arranged on the face 214, so long as the majority of the light sources 230 are disposed within the proximal face portion 272. With the same limitation, it will also be appreciated that the face 214 may comprise any number of mounting surfaces, although only three mounting surfaces are shown in FIGS. 1–4.

Figure 3:
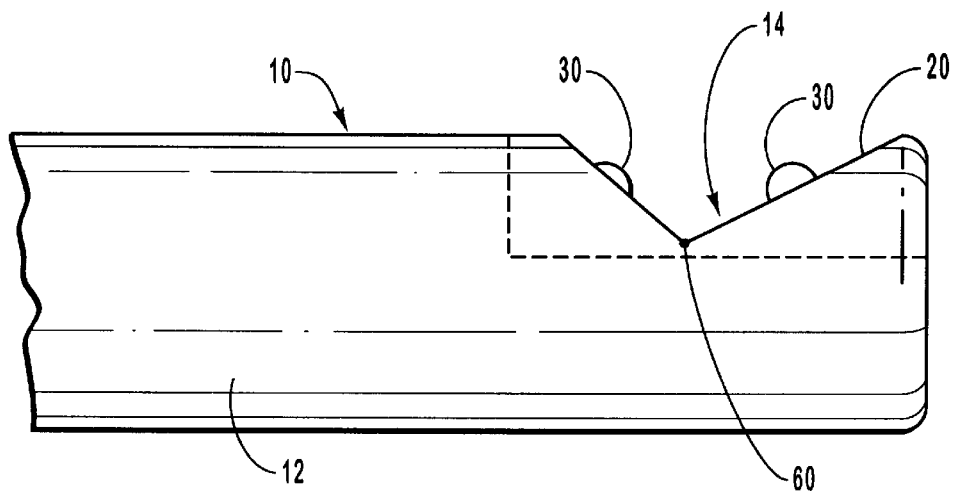
FIG. 3 illustrates a side view of the heat sink shown in FIG. 1.

FIG. 3 illustrates a side view of the heat sink 10 of FIG. 1. As shown in FIGS. 1 and 3, the face 14 of the heat sink 10 is recessed and generally concaved within the body 12 of the heat sink 10. This concavity results from the convergence of the three mounting surfaces 20–24 at a recessed intersection point 60. The recessed intersection point 260 is also illustrated in FIG. 2 as the location where mounting surfaces 220, 224 converge.

As shown in FIG. 1, the concavity of the face 14 can generally be defined by the surface-to-surface angles 80 that occur between the different mounting surfaces 20, 22, 24. It will also be appreciated that the surface-to-surface angles 80 between the mounting surfaces 20, 22, 24 control the angle at which the light is emitted from the light sources 30. According to one presently preferred embodiment, in order to create a desired illumination foot print from the light sources, each of the surface-to-surface angles 80 between the mounting surfaces 20, 22, 24 comprise the same angle, within the range of about 100° and 140°, with a preferred angle of about 120°. It will be appreciated, however, that any suitable surface-to-surface angle may be used. It will also be appreciated that the mounting surfaces 20, 22, 24 can be curved, in which case the surface-to-surface angles 80 may vary significantly.

Turning now to FIG. 4, one alternative embodiment of the heat sink 410 of the invention is shown. According to this embodiment, the heat sink 410 comprises a small semi-circular body 412 that is configured for being mounted on the flat surface 490 of another object, such as secondary heat sink 492. This embodiment may be preferred, for example, when the heat sink 410 is composed of an expensive alloy or when the secondary heat sink 492 is integrally connected to a dental light-curing device. This embodiment is also useful when mounting or otherwise securing the light sources 430 from the bottom of the heat sink 410.

In summary, the heat sinks of the invention generally provide arrangements of mounting surfaces and corresponding light sources that are geometrically configured to minimize the heat that is generated at the distal ends of the heat sinks. The geometric arrangements of the mounting surfaces also expedites the conduction of heat away from the light sources, thereby maximizing the efficiency of the heat sinks.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A heat sink for a dental light-curing device comprising:
    a body extending between a proximal end and a distal end; and
    a face located near the distal end of the body and that includes:
        a proximal portion having a length;
        a distal portion having a length equal to the length of the proximal portion; and
        a plurality of mounting surfaces configured for mounting light sources on the face, the mounting surfaces having a combined surface area, wherein a majority of the combined surface area of the mounting surfaces is located in the proximal portion of the face.

2. A heat sink as recited in claim 1, wherein each mounting surface is configured to receive at least one of an LED, an LED array, or a plurality of LEDs.

3. A heat sink as recited in claim 1, wherein each mounting surface is configured for mounting a single LED.

4. A heat sink as recited in claim 1, the heat sink comprising at least one of aluminum, copper, or silver.

5. A heat sink as recited in claim 1, wherein the plurality of mounting surfaces includes a first mounting surface, a second mounting surface, and a third mounting surface, and wherein the first mounting surface is disposed within the distal portion of the face, and wherein at least a majority of the second and third mounting surfaces is disposed within the proximal portion of the face.

6. A heat sink as recited in claim 5, wherein the mounting surfaces define a line of symmetry that forms a boundary between the second and third mounting surfaces and that bisects the first mounting surface.

7. A heat sink as recited in claim 6, wherein the line of symmetry is substantially parallel to a central axis of the heat sink.

8. A heat sink as recited in claim 1, wherein the mounting surfaces converge at a single intersection point.

9. A heat sink as recited in claim 8, wherein the single intersection point is recessed, such that the face is concaved into the body of the heat sink.

10. A heat sink as recited in claim 1, wherein at least a portion of the body of the heat sink comprises a cylindrical cross section.

11. A heat sink as recited in claim 1, wherein a surface-to-surface angle exists between each of the mounting surfaces, and wherein the surface-to-surface angle comprises an angle within a range of about 100° to about 140°.

12. A heat sink as recited in claim 1, wherein each mounting surface is substantially planar.

13. A heat sink as recited in claim 1, wherein the heat sink comprises a planar surface configured for mounting onto a secondary heat sink.

14. A heat sink for a dental light-curing device comprising:
    a body extending between a proximal end and a distal end; and
    a face located near the distal end of the body and including:
        a proximal portion having a length;
        a distal portion having a length equal to the length of the proximal portion; and
        three mounting surfaces configured for mounting a single light source within the distal portion of the face and at least two light sources within the proximal portion of the face.

15. A heat sink as recited in claim 14, wherein each light source comprises at least one of an LED or an LED array.

16. A heat sink as recited in claim 14, wherein the body and the face comprise at least one of aluminum, copper, or silver.

17. A heat sink as recited in claim 14, wherein the face is concaved.

18. A dental light-curing device comprising:
    a heat sink including:
        a body extending between a proximal end and a distal end; and
        a face configured for mounting light sources, the face including a proximal portion and a distal portion having substantially equal lengths, wherein the proximal face portion is configured to mount two light sources and wherein the distal face portion is configured to mount a single light source;
    a single light source mounted on the distal face portion; and
    two light sources mounted on the proximal face portion.

19. A dental light-curing device as recited in claim 18, wherein the light sources comprise at least one of an LED or an LED array.

20. A dental light-curing device as recited in claim 18, wherein the face is symmetrically disposed adjacent to the distal end of the body, such that the two light sources mounted on the proximal face portion are equidistant from the distal end of the body.

21. A heat sink as recited in claim 1, the heat sink comprising at least one metal.

22. A heat sink as recited in claim 14, the heat sink comprising at least one metal.

23. A dental light-curing device as recited in claim 18, the heat sink comprising at least one metal.

24. A dental light-curing device comprising:
    a heat sink including:
        a body extending between a proximal end and a distal end; and
        a face configured for mounting light sources, the face comprising a proximal portion having a length and a distal portion having a length equal to the length of the proximal portion,
    a plurality of light sources mounted on or within the face of the heat sink, a majority of which are disposed within the proximal face portion.

25. A dental light-curing device as recited in claim 24, wherein the light sources comprise a plurality of LEDs having a surface area, wherein the surface area of the LEDs disposed in the proximal face portion exceeds the surface area of the LEDs disposed in the distal face portion.

26. A dental light-curing device as recited in claim 24, wherein the light sources comprise a plurality of LEDs so that the number of LEDs disposed in the proximal face portion exceeds the number of LEDs disposed in the distal face portion.

27. A dental light-curing device as recited in claim 24, wherein the each light source comprises an LED array comprising individual LEDs so that the number of individual LEDs disposed in the proximal face portion exceeds the number of individual LEDs disposed in the distal face portion.

28. A dental light-curing device comprising:
a heat sink including:
  a body extending between a proximal end and a distal end; and
  a face configured for mounting light sources, the face comprising a proximal portion having a length and a distal portion having a length equal to the length of the proximal portion,
a plurality of LEDs mounted on or within the face of the heat sink, the LEDs having a combined surface area, a majority of which is disposed within the proximal face portion.

* * * * *